United States Patent
de Villiers et al.

(10) Patent No.: US 7,442,211 B2
(45) Date of Patent: *Oct. 28, 2008

(54) INTERVERTEBRAL PROSTHETIC DISC

(75) Inventors: Malan de Villiers, Gauteng (ZA); Ulrich Hanle, Johannesburg (ZA)

(73) Assignee: SpinalMotion, Inc., Mountain View, CA (US)

( * ) Notice: Subject to any disclaimer, the term of this patent is extended or adjusted under 35 U.S.C. 154(b) by 261 days.

This patent is subject to a terminal disclaimer.

(21) Appl. No.: 10/855,817

(22) Filed: May 26, 2004

(65) Prior Publication Data

US 2005/0021146 A1    Jan. 27, 2005

Related U.S. Application Data

(60) Provisional application No. 60/473,802, filed on May 27, 2003, provisional application No. 60/473,803, filed on May 27, 2003.

(51) Int. Cl.
A61F 2/44 (2006.01)

(52) U.S. Cl. ................. 623/17.14; 623/17.15

(58) Field of Classification Search .... 623/17.11–17.16
See application file for complete search history.

(56) References Cited

U.S. PATENT DOCUMENTS

| | | | |
|---|---|---|---|
| 3,486,505 A | 12/1969 | Morrison | |
| 4,759,766 A | 7/1988 | Buettner-Janz et al. | |
| 4,759,769 A | 7/1988 | Hedman et al. | |
| 4,834,757 A | 5/1989 | Brantigan | |
| 4,863,477 A | 9/1989 | Monson | |
| 4,997,432 A | 3/1991 | Keller | |
| 5,035,716 A | 7/1991 | Downey | |
| 5,071,437 A | 12/1991 | Steffee | |
| 5,122,130 A | 6/1992 | Keller | |
| 5,195,526 A | 3/1993 | Michelson | |
| 5,258,031 A | 11/1993 | Salib et al. | |
| 5,314,477 A | 5/1994 | Marnay | |
| 5,370,697 A | 12/1994 | Baumgartner | |

(Continued)

FOREIGN PATENT DOCUMENTS

DE    3023353 A1    4/1981

(Continued)

OTHER PUBLICATIONS

Wayne G. Hellier, et al., "Wear Studies for Development of an Intervertebral Disc Prosthesis," *Spine*, (1992) vol. 17 (6), *Supplement* pp. 86-96.

Choon-Ki Lee, MD, et al., "Impact Response of the Intervertebral Disc in a Finite-Element Model," *Spine*, (2000) vol. 25, (1) pp. 2431-2439.

(Continued)

*Primary Examiner*—Bruce E. Snow
(74) *Attorney, Agent, or Firm*—Townsend and Townsend and Crew LLP

(57) ABSTRACT

A prosthetic disc for insertion between adjacent vertebrae includes upper and lower plates, a core disposed between the plates, and at least one projection extending from at least one of the upper and lower curved surfaces of the core into at least one recess of one of the inner surfaces of the plates. The recess is oversize with respect to the projection to allow sliding movement of the plate over the core while retaining the core between the plates during such sliding movement. The projection(s) may include a rod extending through an axial hole in the core, multiple surface features of the core, or the like.

22 Claims, 6 Drawing Sheets

U.S. PATENT DOCUMENTS

| | | | |
|---|---|---|---|
| 5,401,269 A | 3/1995 | Buettner-Janz et al. | |
| 5,415,704 A | 5/1995 | Davidson | |
| 5,507,816 A * | 4/1996 | Bullivant | 623/17.15 |
| 5,534,030 A | 7/1996 | Navarro et al. | |
| 5,556,431 A | 9/1996 | Buttner-Janz | |
| 5,674,296 A | 10/1997 | Bryan et al. | |
| 5,676,701 A | 10/1997 | Yuan et al. | |
| 5,676,702 A | 10/1997 | Ratron | |
| 5,702,450 A | 12/1997 | Bisserie | |
| 5,797,909 A | 8/1998 | Michelson | |
| 5,824,094 A | 10/1998 | Serhan et al. | |
| 5,865,846 A | 2/1999 | Bryan et al. | |
| 5,888,226 A | 3/1999 | Rogozinski | |
| 5,899,901 A | 5/1999 | Middleton | |
| 5,899,911 A | 5/1999 | Carter | |
| 5,989,291 A | 11/1999 | Ralph et al. | |
| 6,001,130 A | 12/1999 | Bryan et al. | |
| 6,019,792 A | 2/2000 | Cauthen | |
| 6,022,376 A | 2/2000 | Assell et al. | |
| 6,039,763 A | 3/2000 | Shelokov | |
| 6,096,038 A | 8/2000 | Michelson | |
| 6,139,579 A | 10/2000 | Steffee et al. | |
| 6,146,421 A | 11/2000 | Gordon et al. | |
| 6,156,067 A | 12/2000 | Bryan et al. | |
| 6,162,252 A | 12/2000 | Kuras et al. | |
| 6,235,030 B1 | 5/2001 | Zucherman et al. | |
| 6,261,296 B1 | 7/2001 | Aebi et al. | |
| 6,315,797 B1 | 11/2001 | Middleton | |
| 6,348,071 B1 | 2/2002 | Steffee et al. | |
| 6,368,350 B1 | 4/2002 | Erickson et al. | |
| 6,416,551 B1 | 7/2002 | Keller | |
| 6,447,544 B1 * | 9/2002 | Michelson | 623/17.16 |
| 6,478,800 B1 | 11/2002 | Fraser et al. | |
| 6,517,580 B1 | 2/2003 | Ramadan et al. | |
| 6,562,047 B2 | 5/2003 | Ralph et al. | |
| 6,592,624 B1 | 7/2003 | Fraser et al. | |
| 6,599,294 B2 | 7/2003 | Fuss et al. | |
| 6,607,558 B2 | 8/2003 | Kuras | |
| 6,610,092 B2 | 8/2003 | Ralph et al. | |
| 6,645,248 B2 | 11/2003 | Casutt | |
| 6,652,533 B2 | 11/2003 | O'Neil | |
| 6,666,866 B2 | 12/2003 | Mertz et al. | |
| 6,669,732 B2 | 12/2003 | Serhan et al. | |
| 6,682,562 B2 | 1/2004 | Viart et al. | |
| 6,689,132 B2 | 2/2004 | Biscup | |
| 6,706,068 B2 | 3/2004 | Ferree | |
| 6,712,825 B2 | 3/2004 | Aebi et al. | |
| 6,726,720 B2 | 4/2004 | Ross et al. | |
| 6,740,118 B2 | 5/2004 | Eisermann et al. | |
| 6,770,095 B2 | 8/2004 | Grinberg et al. | |
| 6,814,737 B2 | 11/2004 | Cauthen | |
| 6,875,213 B2 | 4/2005 | Michelson | |
| 6,963,071 B2 | 11/2005 | Bristol | |
| 6,966,929 B2 | 11/2005 | Mitchell | |
| 7,025,787 B2 | 4/2006 | Bryan et al. | |
| 7,056,344 B2 * | 6/2006 | Huppert et al. | 623/17.16 |
| 7,179,294 B2 | 2/2007 | Eisermann et al. | |
| 2001/0016773 A1 | 8/2001 | Serhan et al. | |
| 2001/0029377 A1 | 10/2001 | Aebi et al. | |
| 2002/0035400 A1 | 3/2002 | Bryan et al. | |
| 2002/0045904 A1 | 4/2002 | Konstantin et al. | |
| 2002/0128715 A1 | 9/2002 | Bryan et al. | |
| 2002/0198532 A1 | 12/2002 | Michelson | |
| 2003/0009224 A1 | 1/2003 | Kuras | |
| 2003/0074076 A1 | 4/2003 | Ferree et al. | |
| 2003/0100951 A1 | 5/2003 | Serhan et al. | |
| 2003/0135277 A1 | 7/2003 | Bryan et al. | |
| 2003/0191536 A1 | 10/2003 | Ferree | |
| 2003/0199982 A1 | 10/2003 | Bryan | |
| 2003/0204261 A1 | 10/2003 | Eisermann et al. | |
| 2003/0208271 A1 | 11/2003 | Kuras | |
| 2004/0002761 A1 | 1/2004 | Rogers et al. | |
| 2004/0024407 A1 | 2/2004 | Ralph | |
| 2004/0030391 A1 | 2/2004 | Ferree | |
| 2004/0073312 A1 | 4/2004 | Eisermann et al. | |
| 2004/0143270 A1 | 7/2004 | Zucherman et al. | |
| 2004/0176843 A1 | 9/2004 | Zubok et al. | |
| 2005/0021145 A1 | 1/2005 | de Villiers et al. | |
| 2005/0021146 A1 | 1/2005 | de Villiers et al. | |
| 2005/0043800 A1 | 2/2005 | Paul et al. | |
| 2005/0085917 A1 | 4/2005 | Marmay et al. | |
| 2005/0107881 A1 | 5/2005 | Alleyne et al. | |
| 2005/0149189 A1 | 7/2005 | Mokhtar et al. | |
| 2005/0192586 A1 | 9/2005 | Zuckerman et al. | |
| 2005/0192670 A1 | 9/2005 | Zubok et al. | |
| 2005/0197706 A1 | 9/2005 | Hovorka et al. | |
| 2005/0251262 A1 | 11/2005 | de Villiers et al. | |
| 2005/0261772 A1 | 11/2005 | Filippi et al. | |
| 2005/0267580 A1 * | 12/2005 | Suddaby | 623/17.12 |
| 2006/0004453 A1 | 1/2006 | Bartish et al. | |
| 2006/0025862 A1 | 2/2006 | de Villiers et al. | |
| 2006/0036325 A1 | 2/2006 | Paul et al. | |
| 2006/0041313 A1 | 2/2006 | Allard et al. | |
| 2006/0069439 A1 | 3/2006 | Zucherman et al. | |
| 2006/0293754 A1 | 12/2006 | de Villiers et al. | |
| 2007/0061011 A1 | 3/2007 | de Villiers et al. | |

FOREIGN PATENT DOCUMENTS

| | | |
|---|---|---|
| EP | 0333990 A2 | 9/1989 |
| EP | 0560140 A1 | 9/1993 |
| EP | 0560141 A1 | 9/1993 |
| EP | 1142544 A1 | 10/2001 |
| EP | 1153582 A2 | 11/2001 |
| EP | 1250898 A1 | 10/2002 |
| EP | 1306064 A1 | 5/2003 |
| EP | 1344493 A1 | 9/2003 |
| EP | 1344506 A1 | 9/2003 |
| EP | 1344507 A1 | 9/2003 |
| EP | 1344508 A1 | 9/2003 |
| EP | 1417940 A1 | 5/2004 |
| WO | WO 00/35384 | 6/2000 |
| WO | WO 01/01893 A1 | 1/2001 |
| WO | 2004026187 A | 4/2004 |
| WO | 2005053580 A1 | 6/2005 |
| ZA | 03/9312 | 11/2003 |

OTHER PUBLICATIONS

J.C. Le Huec, "Shock Absorption in Lumbar Disc Prosthesis," *Journal of Spinal Disorders & Techniques*, vol. 16 (4) pp. 346-351, no date.

International Search Report for PCT/US05/26160.

Büttner-Janz, Karin, "The Development of the Artificial Disc," SB Charite—Hundley & Associates, TX (1992).

* cited by examiner

INTERVERTEBRAL PROSTHETIC DISC

CROSS-REFERENCES TO RELATED APPLICATIONS

This application claims the priority of U.S. Provisional Patent Application Ser. Nos. 60/473,802, entitled "Prosthetic Disc for Intervertebral Insertion," and 60/473,803, entitled "Intervertebral Prosthetic Disc," both of which were filed May 27, 2003, the full disclosures of which are hereby incorporated by reference.

BACKGROUND OF THE INVENTION

1. Field of the Invention

This invention relates to medical devices and methods. More specifically, the invention relates to a prosthetic disc for intervertebral insertion, such as in the lumbar and cervical spine.

In the event of damage to a lumbar or cervical intervertebral disc, one possible surgical treatment is to replace the damaged disc with a disc prosthesis. Several types of intervertebral disc prostheses are currently available. For example, one type of intervertebral disc prosthesis is provided by Waldemar Link GmbH & Co under the trademark LINK® SB Charite. This prosthesis includes upper and lower prosthesis plates or shells which locate against and engage the adjacent vertebral bodies, and a low friction core between the plates. The core has upper and lower convexly curved surfaces and the plates have corresponding, concavely curved recesses which cooperate with the curved surfaces of the core. This allows the plates to slide over the core to allow required spinal movements to take place. The curved recesses in the plates are surrounded by annular ridges which locate, at the limit of sliding movement of the plates over the core, in opposing upwardly and downwardly facing, peripheral channels surrounding the curved surfaces of the core.

This type of disc configuration is described in EP 1142544A1 and EP 1250898A1, assigned to Waldemar Link GmbH & Co. A drawback of such configurations is that the provision of the peripheral ribs and channels limits the areas available for bearing and sliding contact between the plates and core, and accordingly the loads which can be transmitted by the prosthesis. As a result of the relatively small bearing areas, it is believed that at least the core will be subject to rapid wear and have a relatively short lifespan. Also, because the core is in effect merely "clamped" between the plates, this configuration does not allow for secure retention of the core. In one alternative arrangement, the curved surfaces of the core carry opposing, elongate keys that locate in elongate grooves in the plates and another alternative arrangement in which the plates have opposing elongate keys that locate in elongate grooves in the opposite curved surfaces of the core. These key and groove arrangements allow the plates to slide over the core within the limits of the length of the grooves, in one direction only. Although allowance is made for some lateral play of the keys in the grooves, very little sliding movement of the plates over the core can take place in the orthogonal vertical plane, and this is considered to be a serious drawback of this design.

Other currently available intervertebral disc prostheses have similar and/or other drawbacks. Typically, drawbacks include insufficient resistance to wear and tear, restricted range of motion and/or insufficient ability of the prosthesis to adhere to vertebral bone.

Therefore, a need exists for improved intervertebral disc prostheses. Ideally, such improved prostheses would resist wear and tear, provide a desired range of motion and adhere well to vertebral bone. At least some of these objectives will be met by the present invention.

2. Description of the Background Art

Published U.S. patent applications 2002/0035400A1 and 2002/0128715A1 describe disc implants which comprise opposing plates with a core between them over which the plates can slide. The core receives one or more central posts, which are carried by the plates and which locate in opposite ends of a central opening in the core. Such arrangements limit the load bearing area available between the plates and core.

Other patents related to intervertebral disc prostheses include U.S. Pat. Nos. 4,759,766; 4,863,477; 4,997,432; 5,035,716; 5,071,437; 5,370,697; 5,401,269; 5,507,816; 5,534,030; 5,556,431; 5,674,296; 5,676,702; 5,702,450; 5,824,094; 5,865,846; 5,989,291; 6,001,130; 6,022,376; 6,039,763; 6,139,579; 6,156,067; 6,162,252; 6,315,797; 6,348,071; 6,368,350; 6,416,551; 6,592,624; 6,607,558 and 6,706,068. Other patent applications related to intervertebral disc prostheses include U.S. patent application Publication Nos.: 2003/0009224; 2003/0074076; 2003/0191536; 2003/0208271; 2003/0135277; 2003/0199982; 2001/0016773 and 2003/0100951. Other related patents include WO 01/01893A1, EP 1344507, EP 1344506, EP 1250898, EP 1306064, EP 1344508, EP 1344493, EP 1417940, EP 1142544, and EP 0333990.

BRIEF SUMMARY OF THE INVENTION

In one aspect of the present invention, an intervertebral prosthetic disc for insertion between adjacent vertebrae comprises: upper and lower plates having outer surfaces locatable against the respective vertebrae and inner, curved surfaces; a core between the plates, the core having upper and lower curved surfaces complementary in shape to the inner, curved surfaces of the plates to allow the plates to slide over the core; and at least one projection extending from at least one of the upper and lower curved surfaces of the core into at least one recess of one of the inner surfaces of the plates, the recess being oversize with respect to the projection to allow sliding movement of the plate over the core while retaining the core between the plates during such sliding movement.

Some embodiments further include multiple projections extending from the upper and lower surfaces of the core. For example, the multiple projections may include two elevated rings projecting from a peripheral portion of each of the upper and lower surfaces of the core into ring-shaped recesses on the upper and lower plates. In other embodiments, the multiple projections may comprise multiple surface features projecting from a peripheral portion of each of the upper and lower surfaces of the core into multiple recesses on the upper and lower plates. In yet other embodiments, the multiple projections may comprise respective ends of an elongate, upright element extending axially through the core, the ends projecting beyond the upper and lower core surfaces. For example, the upright element may comprise a rod extending through an axial passage through the core. In some embodiments, such a rod and passage may be complementarily threaded for engagement with one another.

In some embodiments, the disc further includes at least one fin extending from each of the outer surfaces of the plates to promote attachment of the plates to the vertebrae. In some embodiments, each fin extends from its respective outer surface at a 90° angle. In other embodiments, each fin extends from its respective outer surface at an angle other than 90°. In some embodiments, each fin includes at least one hole for promoting attachment of the plates to the vertebrae. For further promoting attachment of the plates to the vertebrae some embodiments include outer surfaces of the plates that are textured. For example, in some embodiments the textured surfaces comprise multiple serrations.

The plates may have any of a number of different configurations, sizes, or the like. In one embodiment, the outer surfaces of the plates are flat. In one embodiment, lateral edge portions of the upper and lower plates are adapted to contact one another during sliding movement of the plates over the core.

In another aspect of the present invention, an intervertebral prosthetic disc for insertion between adjacent vertebrae comprises: upper and lower plates having outer surfaces locatable against the respective vertebrae and inner, curved surfaces, at least one of the inner surfaces having at least one recess; a core between the plates, the core having upper and lower curved surfaces complementary in shape to the inner, curved surfaces of the plates to allow the plates to slide over the core, and an axial passage extending through the core; and a rod extending through the axial passage into the at least one recess in the inner surface(s) of the plate(s). The recess are oversize with respect to the projection to allow sliding movement of the plate over the core while retaining the core between the plates during such sliding movement.

Optionally, the rod and passage may be complementarily threaded for engagement with one another. In some embodiments, the rod is movably engaged with a first oversized recess on the upper plate and a second oversized recess on the lower plate. In various embodiments, the plates and core may have any of the features or characteristics described above.

In another aspect of the invention, an intervertebral prosthetic disc for insertion between adjacent vertebrae includes: upper and lower plates having outer surfaces locatable against the respective vertebrae and inner, curved surfaces; a core between the plates, the core having upper and lower curved surfaces complementary in shape to the inner, curved surfaces of the plates to allow the plates to slide over the core; and a flexible tie member extending laterally through the core and having ends outside the core which are engaged with one or both of the plates to retain the core between the plates when the plates slide over the core. The flexible tie member, for example, may extend through a lateral passage through the core and may include ends engaged with at least one of the upper and lower plates. In some embodiments, the flexible tie member comprises a flexible cable or cord.

In yet another example of the present invention, an intervertebral prosthetic disc for insertion between adjacent vertebrae comprises: upper and lower plates having textured outer surfaces locatable against the respective vertebrae, each of the outer surfaces having at least one vertical fin and an edge portion adapted to contact a corresponding edge portion of the other plate, and inner, curved surfaces; and a core between the plates, the core having upper and lower curved surfaces complementary in shape to the inner, curved surfaces of the plates to allow the plates to slide over the core. The curved surfaces of the plates and core include formations which cooperate with one another to retain the core between the plates when the plates slide over the core. The formations include recesses and projections received by the recesses, and the recesses and projections are located between a central axis of the relevant curved surface and an outer periphery thereof.

In some embodiments, for example, the projections may comprise two elevated rings projecting from a peripheral portion of each of the upper and lower surfaces of the core into ring-shaped recesses on the upper and lower plates. In other embodiments, the projections may comprise multiple surface features projecting from a peripheral portion of each of the upper and lower surfaces of the core into multiple recesses on the upper and lower plates. Again, the plates and core may include any of the features described above.

These and other aspects and embodiments are described more fully below with reference to the drawing figures.

DETAILED DESCRIPTION OF THE INVENTION

Figure 1:
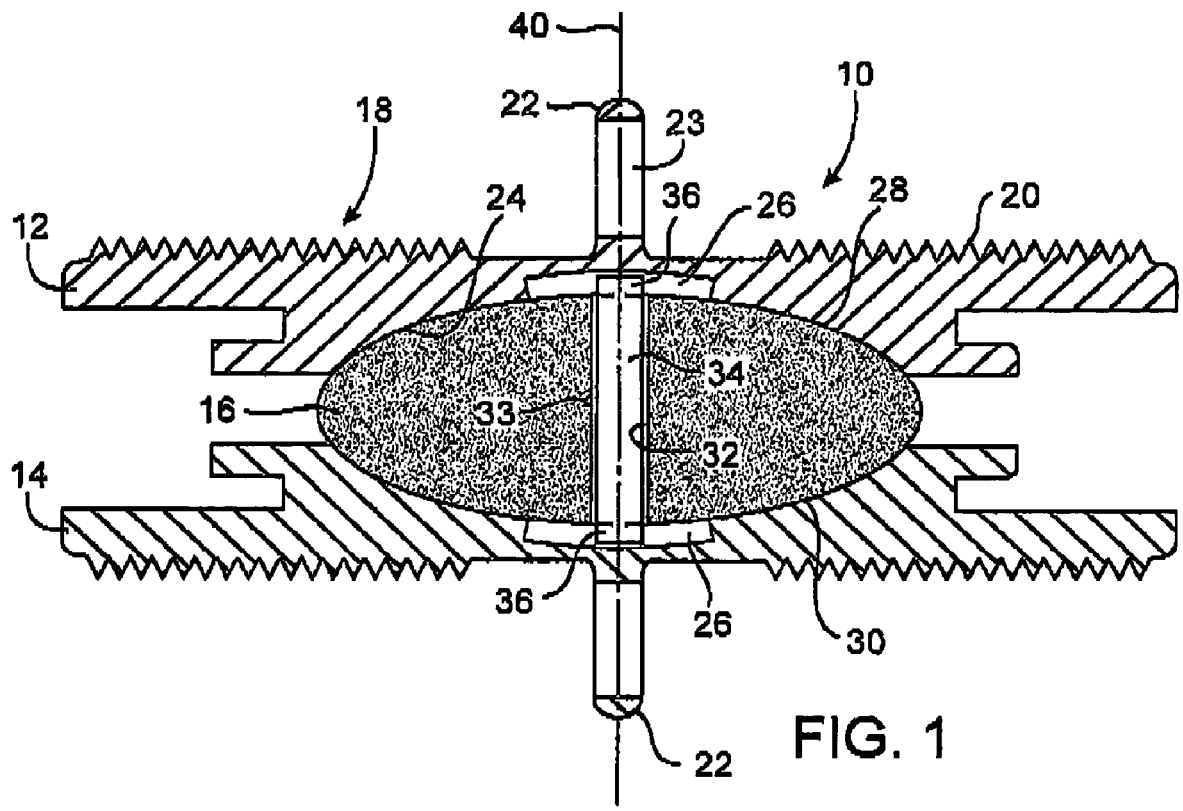
FIG. 1 shows a cross-sectional anterior view of a prosthetic disc according to one embodiment of the invention, with the prosthesis plates and core in vertical alignment.

FIGS. 1-4 illustrate a prosthetic disc 10 for intervertebral insertion between two adjacent spinal vertebrae (not shown). The disc 10 comprises three components, namely an upper plate or shell 12, a lower plate or shell 14 and a core 16 located between the plates.

The upper plate 12 includes an outer surface 18 and an inner surface 24 and may be constructed from any suitable material or combination of materials, such as but not limited to cobalt chrome molybdenum, titanium (such as grade 5 titanium) and/or the like. In one embodiment, typically used in the lumbar spine, the upper plate 12 is constructed of cobalt chrome molybdenum, and the outer surface 18 is treated with aluminum oxide blasting followed by a titanium plasma spray. In another embodiment, typically used in the cervical spine, the upper plate 12 is constructed of titanium, the inner surface 24 is coated with titanium nitride, and the outer surface 18 is treated with aluminum oxide blasting. An alternative cervical spine embodiment includes no coating on the inner surface 24. In some embodiments, it may be useful to couple two materials together to form the inner surface 24 and the outer surface 18. For example, the upper plate 12 may be made of an MRI-compatible material, such as titanium, but may include a harder material, such as cobalt chrome molybdenum, for the inner surface 24. Any suitable technique may be used to couple materials together, such as snap fitting, slip fitting, lamination, interference fitting, use of adhesives, welding and/or the like. Any other suitable combination of materials and coatings may be employed in various embodiments of the invention.

Figure 6:
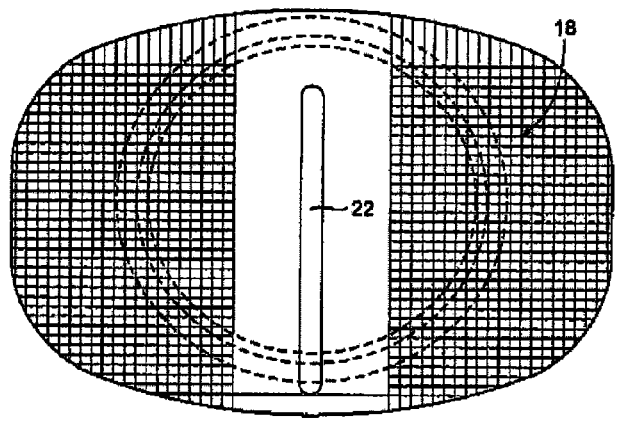
FIG. 6 shows a plan view of the upper plate of the disc of FIG. 1.

In some embodiments, the outer surface 18 is planar. Oftentimes, the outer surface 18 will include one or more surface features and/or materials to enhance attachment of the prosthesis 10 to vertebral bone. For example, the outer surface 18 may be machined to have a serrations 20 or other surface features for promoting adhesion of the upper plate 12 to a vertebra. In the embodiment shown (FIG. 6), the serrations 20 extend in mutually orthogonal directions, but other geometries would also be useful. Additionally, the outer surface 18 may be provided with a rough microfinish formed by blasting with aluminum oxide microparticles or the like. In some embodiments, the outer surface may also be titanium plasma sprayed to further enhance attachment of the outer surface 18 to vertebral bone.

Figure 6A:
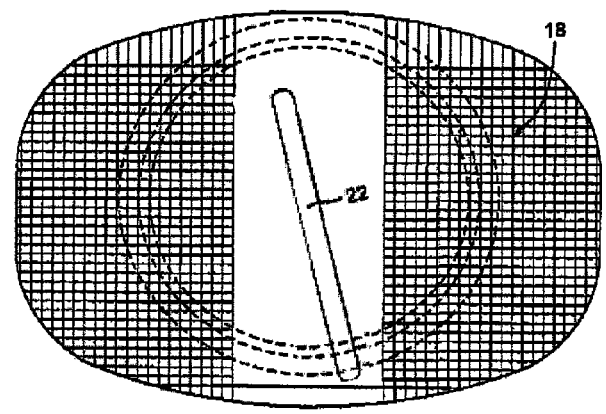
FIG. 6A shows a plan view of a disc, as in FIGS. 1 and 6, with a fin rotated away from the anterior-posterior axis.

The outer surface 18 may also carry an upstanding, vertical fin 22 extending in an anterior-posterior direction. The fin 22 is pierced by transverse holes 23. In an alternative embodiment, as shown in FIG. 6A, the fin 22 may be rotated away from the anterior-posterior axis, such as in a lateral-lateral orientation, a posterolateral-anterolateral orientation, or the like. In some embodiments, the fin 22 may extend from the surface 18 at an angle other than 90°. Furthermore, multiple fins 22 may be attached to the surface 18 and/or the fin 22 may have any other suitable configuration, in various embodiments. In some embodiments, such as discs 10 for cervical insertion, the fins 22, 42 may be omitted altogether.

The lower plate 14 is similar to the upper plate 12 except for the absence of the peripheral restraining structure 26. Thus, the lower plate 14 has an outer surface 40 which is planar, serrated and microfinished like the outer surface 18 of the upper plate 12. The lower plate 14 optionally carries a fin 42 similar to the fin 22 of the upper plate. The inner surface 44 of the lower plate 14 is concavely, spherically curved with a radius of curvature matching that of the inner surface 24 of the upper plate 12. Once again, this surface may be provided with a titanium nitride or other finish.

The core 16 of the disc 10 is made of a low-friction material, such as polyethylene (Chirulen™). In alternative embodiments, the core 16 may comprise any other suitable material, such as other polymers, ceramics or the like. For wear resistance, the surface zones of the core 16 may be hardened by an appropriate cross-linking procedure. A passage 32 extends axially through the core. The passage is provided with an internally threaded sleeve 33 of titanium or other suitable material. An elongate element in the form of a round cross-section, threaded rod 34 extends axially through the passage and is in threaded engagement with the sleeve 33. The length of the rod is greater than the axial dimension of the core, with the result that the opposite ends 36 of the rod project from the curved surfaces 28 and 30 of the core. In the assembled disc 10, these ends 36 locate in the recesses 26. The diameter of the rod is less than that of the recesses 26 so there is substantial room for the rod ends to move laterally in the recesses.

In use, the disc 10 is surgically implanted between adjacent spinal vertebrae in place of a damaged disc. The adjacent vertebrae are forcibly separated from one another to provide the necessary space for insertion. The disc is inserted, normally in a posterior direction, into place between the vertebrae with the fins 22, 42 of the plates 12, 14 entering slots cut in the opposing vertebral surfaces to receive them. After insertion, the vertebrae, facets, adjacent ligaments and soft tissues are allowed to move together to hold the disc in place. The serrated and microfinished surfaces 18, 40 of the plates 12, 14 locate against the opposing vertebrae. The serrations 20 and fins 22, 42 provide initial stability and fixation for the disc 10. With passage of time, enhanced by the titanium surface coating, firm connection between the plates and the vertebrae will be achieved as bone tissue grows over the serrated surface. Bone tissue growth will also take place about the fins 22, 40 and through the transverse holes 23 therein, further enhancing the connection which is achieved.

Figure 5:
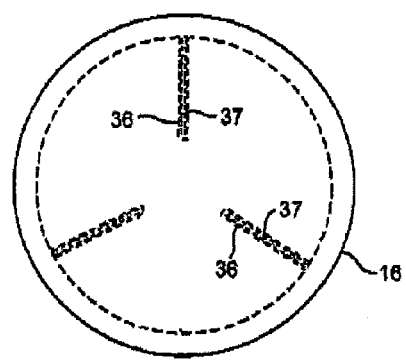
FIG. 5 shows a plan view of the core of the disc of FIG. 1.

Referring to FIG. 5, the core 16 may be formed with narrow, angularly spaced, blind passages 61 which accommodate titanium pins 64. In many embodiments, the core 16 itself is transparent to X-radiation and so is invisible in a post-operative X-ray examination. The pins 64 serve as radiographic markers and enable the position of the core 16 to be ascertained during such examination.

Figure 2:
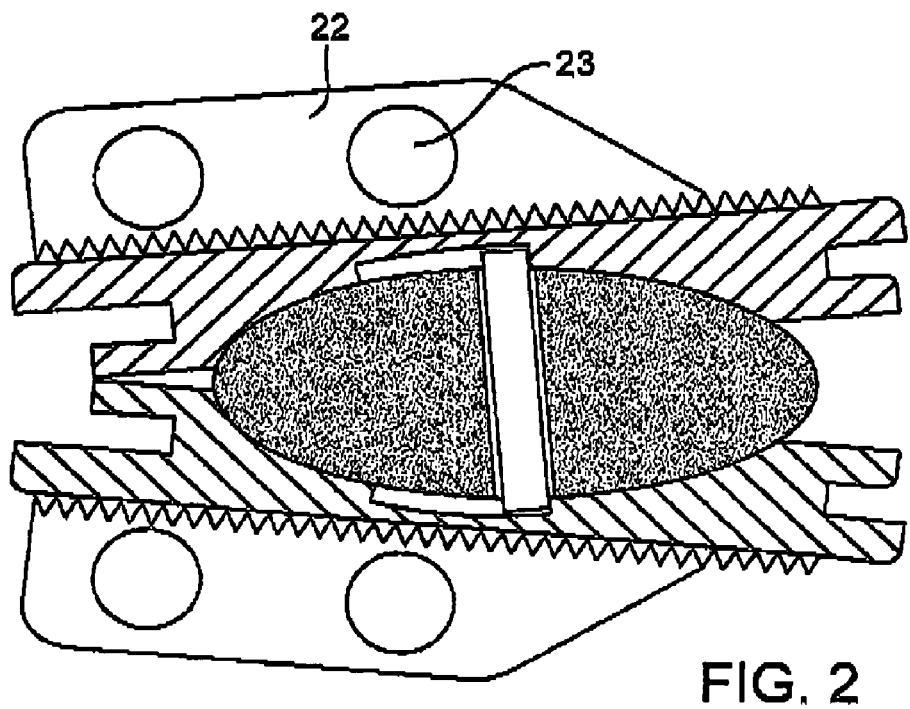
FIG. 2 shows a cross-sectional side view of the disc of FIG. 1, after sliding movement of the plates over the core.
Figure 4:
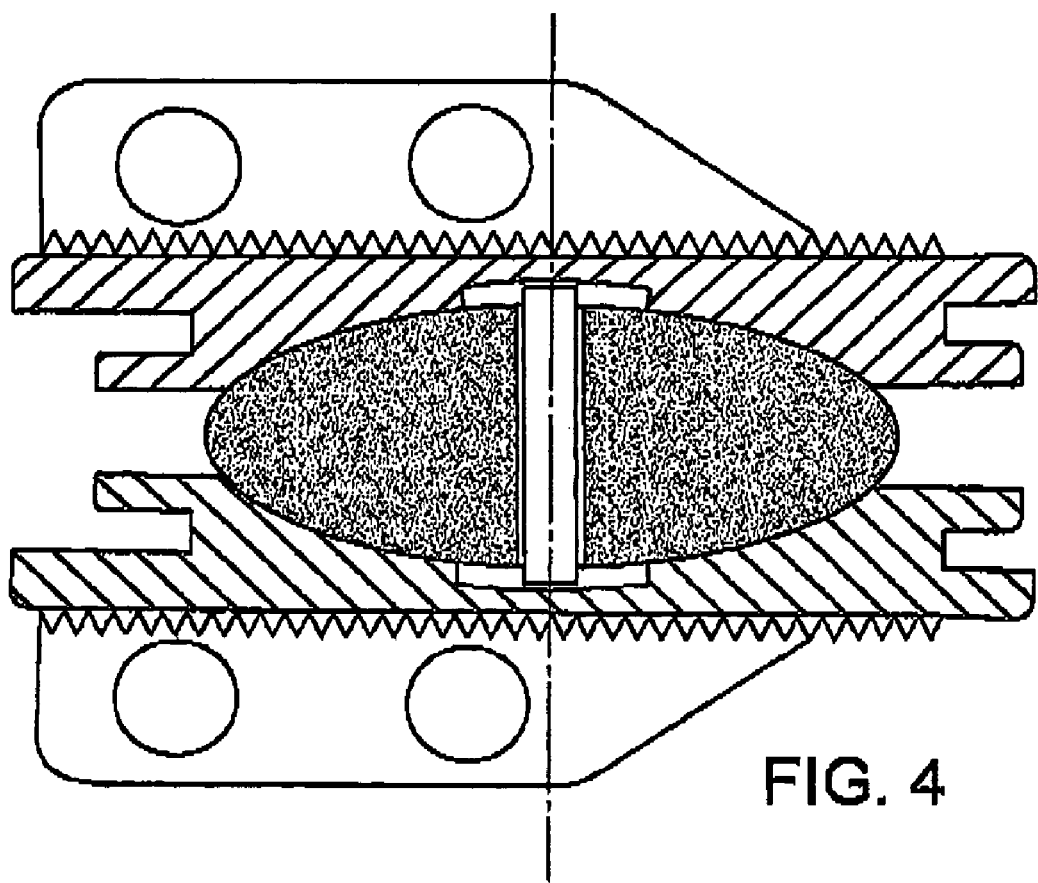
FIG. 4 shows a cross-sectional side view of the disc of FIG. 1, with the plates and core in vertical alignment.

In the assembled disc 10, the complementary and cooperating spherical surfaces of the plates and core allow the plates to slide or articulate over the core through a fairly large range of angles and in all directions or degrees of freedom, including rotation about the central axis 40. FIGS. 1 and 4 show the disc 10 with the plates 12, 14 and core 16 aligned vertically with one another on the axis 40. FIG. 2 illustrates a situation where maximum anterior flexion of the disc has taken place. Such flexion is enabled by the ability of the ends 36 of the rod to move laterally in all directions and through a fairly large distance, in the recesses 26. At the position of maximum flexion, the ends 36 of the rod abut the sides of the recesses as illustrated. At the same time, the plates 12, 14 abut one another at the periphery of their curved surfaces. Similar principles apply to maximum posterior flexure of the plates 12, 14 over the core, i.e. during spinal extension and/or in the event of maximum lateral flexure.

Figure 3:
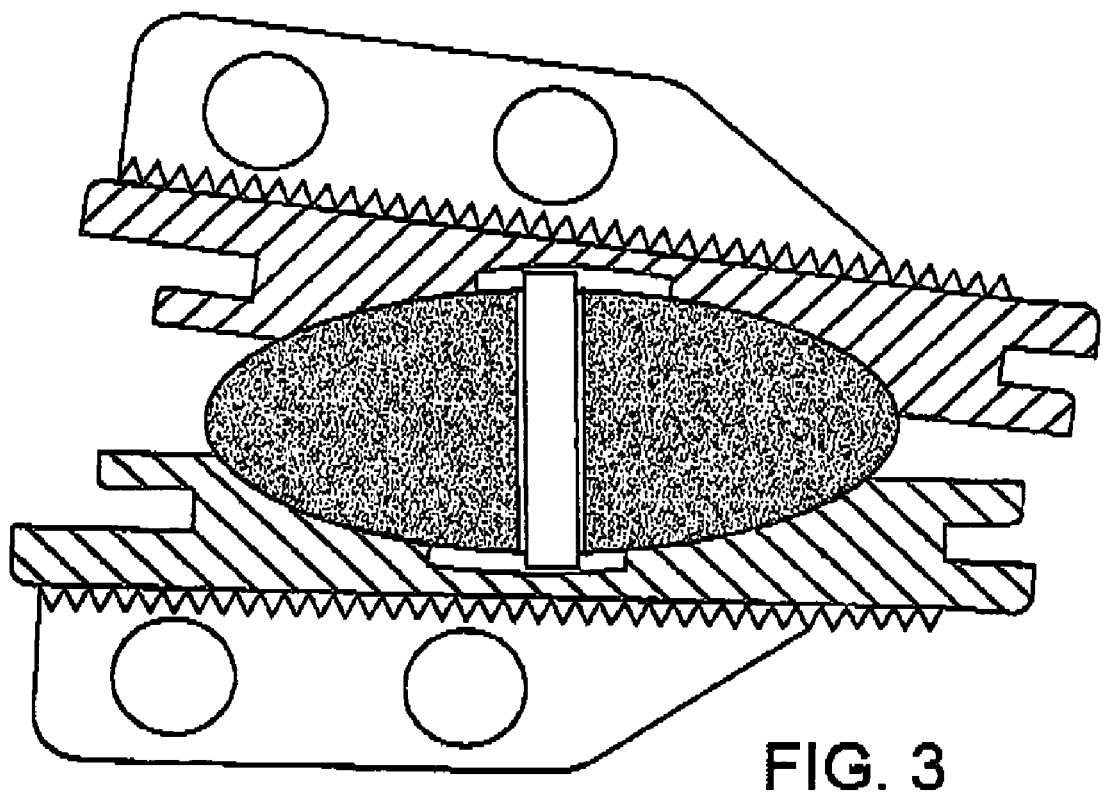
FIG. 3 shows a cross-sectional side view of the disc of FIG. 1, after translational movement of the plates relative to the core.

FIG. 3 illustrates how the disc 10 can also allow for translational movement of the plates relative to the core. In the illustrated situation there has been lateral translation of the plates relative to the core. The limit of lateral translation (not shown) is again reached when the ends 36 of the rod abut laterally against the sides of the recesses 26.

In each case, the cooperating retaining formations, i.e. the ends 36 of the rod and the recesses 26 cooperate with one another to prevent separation of the core from the plates. In other words, the cooperation of the retaining formations ensures that the core is held captive between the plates at all times during flexure of the disc 10. In other embodiments of this version of the invention, the rod can be mounted fixedly to the core by means other than the illustrated threaded connection. In other embodiments, the rod may be replaced by separate elements projecting respectively from the upper and lower curved surfaces of the core.

Figure 7:
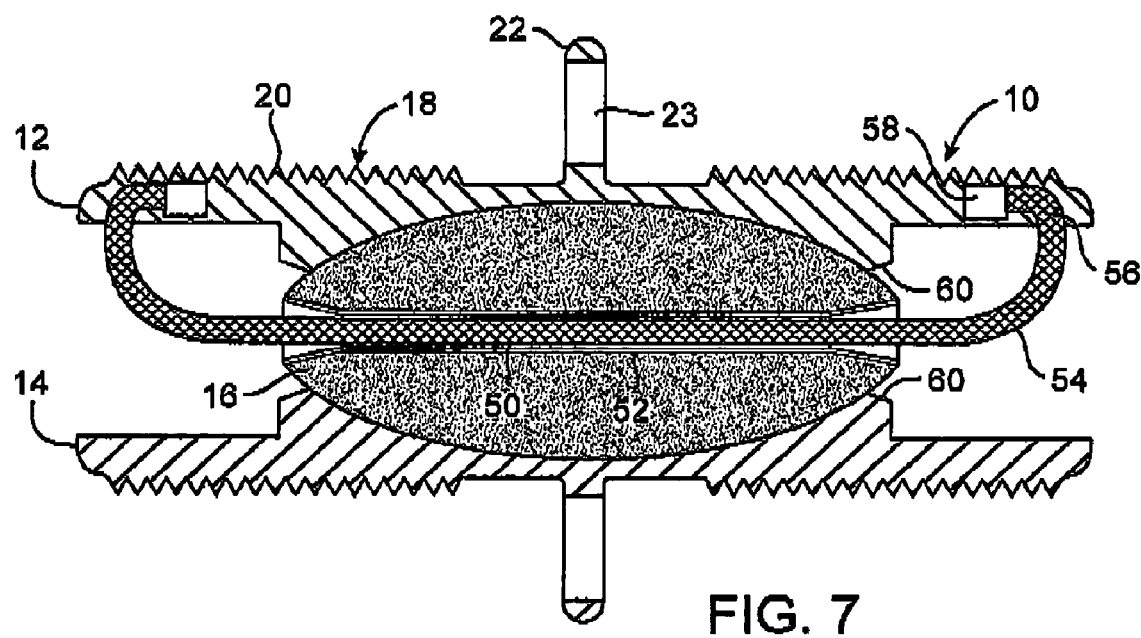
FIG. 7 shows a cross-sectional anterior view of a prosthetic disc according to another embodiment of the invention.
Figure 8:
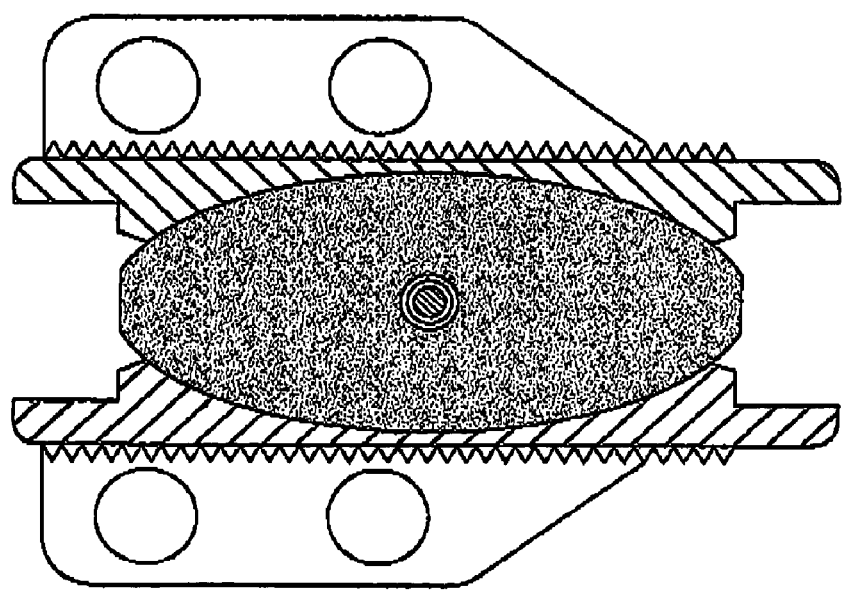
FIG. 8 shows a cross-sectional side view of the prosthetic disc of FIG. 7.

FIGS. 7 and 8 illustrate another embodiment of the invention. In this embodiment, the core 16 is formed with a lateral passage 50 extending diametrically through it. The passage is provided with a sleeve 52 of titanium or other suitably wear resistant material. A flexible tie means, in this embodiment in the form of a cable 54 of braided titanium construction, passes with clearance through the sleeve 52. The ends of the cable 54 are flexed upwardly and enter passages 56 in the upper plate 12. The extremities of the cable carry crimped retention lugs or ferrules 58 anchored in blind ends of the passages 56.

The cable 54 holds the core 16 captive during sliding movement of the plates 12,14 over the core, whether in flexion, extension or translation. The cable can flex through a wide range of angles to allow sliding movement or articulation of the plates relative to the core to take place. The slack in the cable also allows a degree of rotational movement of the plates relative to the core. As illustrated in FIG. 7, the ends of the passage 50 and sleeve 52 are belled to accommodate movements of the cable during sliding movements. Also, surfaces 60 of the plates 12, 14 are inclined to accommodate the cable when sliding has taken place, so that the cable does not act directly on the plates.

Figure 9:
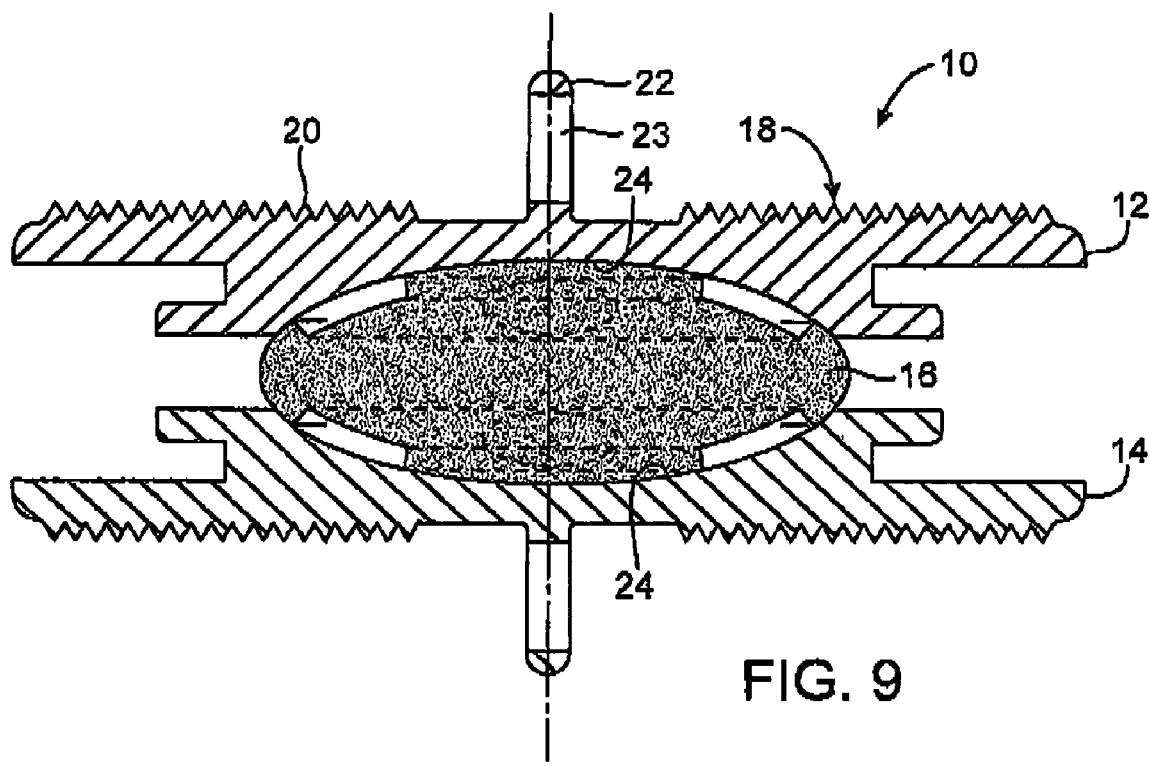
FIG. 9 shows a cross-sectional anterior view of a prosthetic disc according to another embodiment of the invention.
Figure 10:
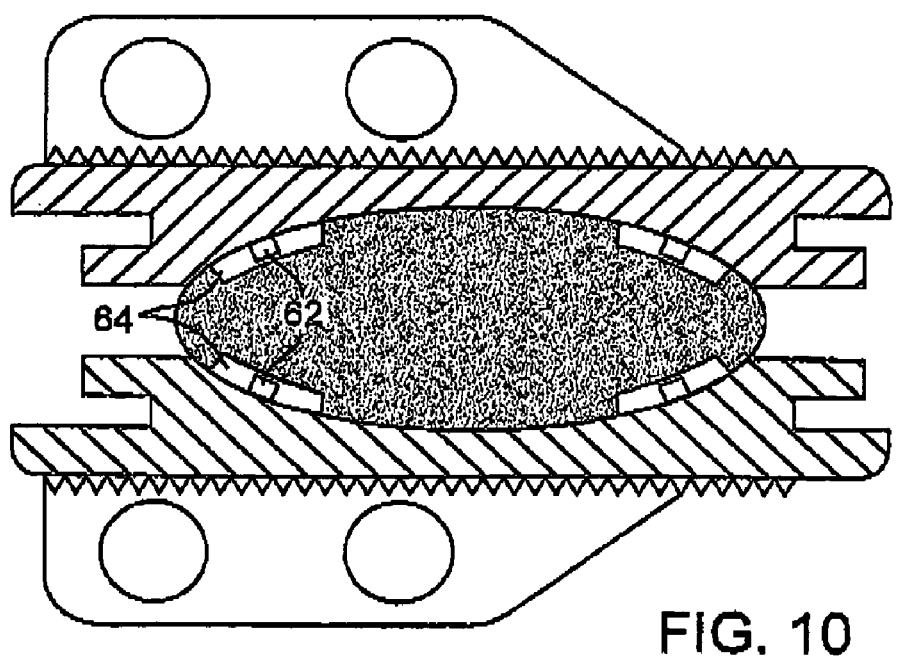
FIG. 10 shows a cross-sectional side view of the prosthetic disc of FIG. 9.

FIGS. 9 and 10 illustrate another embodiment of a prostheses 10. In this embodiment, the curved surfaces 24 of the plates 12, 14 are formed, at positions between the central axis and their peripheries, with continuous, inwardly directed ribs 62 of annular shape. These ribs locate, with considerable clearance, in annular channels 64 provided at corresponding positions in the upper and lower curved surfaces of the core 16. Once again, cooperation between the retaining formations, i.e. the ribs and channels, holds the core captive between the plates when the plates slide over the core during flexion, extension or translation. At the limit of sliding movement in each case, the rib 62 will abut against a side of the channel. The channel may be provided with a wear resistant lining as described previously.

Figure 11:
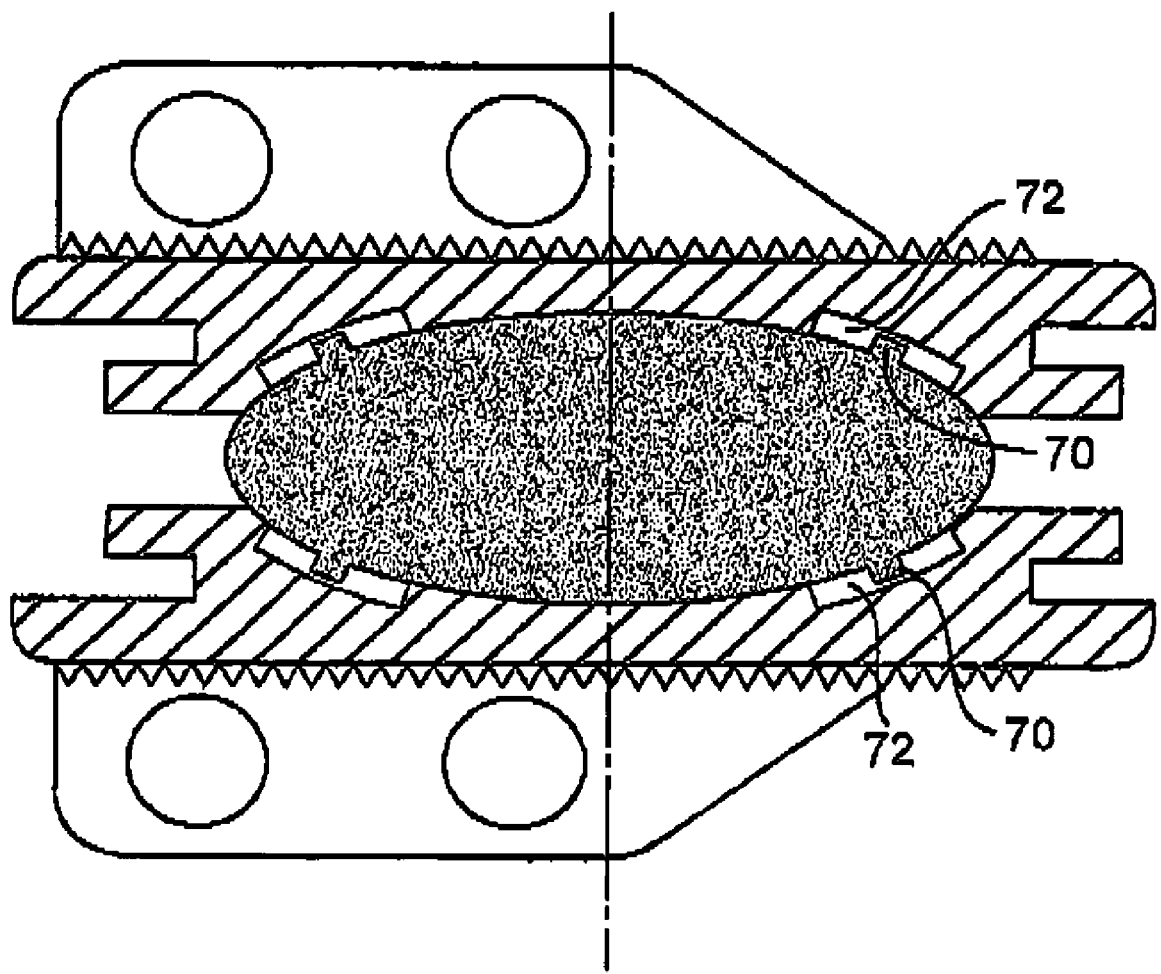
FIG. 11 shows a cross-sectional side view of another embodiment of the invention.

FIG. 11 illustrates another embodiment of a prosthesis. In this case, the core carries continuous, annular ribs 70 on its upper and lower surfaces which locate with clearance in channels 72 in the plates 12, 14. The ribs 70 may be lined with wear resistant material as described previously.

In each of the later versions, i.e. those of FIGS. 7 to 11, the core 16 may be provided with radiographic markers as described previously. Also, in each of these versions, the outer surfaces of the plates 12, 14 may have the same configuration as described in relation to the first version of FIGS. 1 to 6.

In FIGS. 1-6 and 9-11, embodiments are illustrated in which retaining formations are provided that cooperate with one another between both plates and the core. In other embodiments, core retention may be achieved by cooperation between retaining formations which only act between one of the plates, either the upper plate 12 or the lower plate 14, and the core. In one embodiment, for example, there may be a single projection, which extends from the upper (or lower) curved surface of the core and a corresponding recess in the inner surface of the lower (or upper) plate.

Although the foregoing is a complete and accurate description of the invention, any of a number of modifications, additions or the like may be made to the various embodiments without departing from the scope of the invention. Therefore, nothing described above should be interpreted as limiting the scope of the invention at it is described in the claims.

What is claimed is:

1. An intervertebral prosthetic disc for insertion between adjacent vertebrae, the disc comprising:
   upper and lower plates having outer surfaces locatable against the respective vertebrae, inner curved surfaces, and lateral portions;
   a core between the plates, the core having upper and lower curved surfaces complementary in shape to the inner, curved surfaces of the plates to allow the plates to slide over the upper and lower surfaces of the core;
   wherein at least one of the curved surfaces of the plates and at least one of the curved surfaces of the core include annular formations which cooperate with one another to retain the core between the plates when the plates slide over the upper and lower surfaces of the core, such formations including an annular recess and an annular projection received by the recess; and
   wherein the lateral portions of the upper and lower plates are adapted to contact one another during sliding movement of the plates over the core.

2. The prosthetic disc as in claim 1, wherein the recess and the projection-are located between a central axis of the relevant curved surface and an outer periphery thereof.

3. The prosthetic disc as in claim 1, wherein the projection locates within the recess with clearance.

4. The prosthetic disc as in claim 3, wherein at a limit of sliding movement the projection abuts against a side of the recess.

5. The prosthetic disc as in claim 1, further including at least one fin extending from each of the outer surfaces of the plates.

6. The prosthetic disc as in claim 5, wherein each fin is oriented in a straight line in an anterior-posterior direction.

7. The prosthetic disc as in claim 5, wherein each fin is rotated away from an anterior-posterior axis of the disc.

8. The prosthetic disc as in claim 1, wherein the lateral portions of the upper and lower plates comprise lateral edge portions.

9. The prosthetic disc as in claim 1, wherein the outer surfaces of the plates are textured to enhance attachment of the plates to the vertebrae.

10. The prosthetic disc as in claim 9, wherein the textured surfaces comprise multiple serrations.

11. The prosthetic disc as in claim 1 wherein the lateral portions of the upper and lower plates comprise outer peripheries of the curved surfaces and wherein the plates are adapted to contact one another at the outer peripheries of the curved surfaces.

12. An intervertebral prosthetic disc for insertion between adjacent vertebrae, the disc comprising:
    upper and lower plates having outer surfaces locatable against the respective vertebrae, inner curved surfaces, and lateral portions, wherein at least one of the inner curved surfaces of the plates comprises an inwardly directed annular rib;
    a core between the plates, the core having upper and lower curved surfaces complementary in shape to the inner, curved surfaces of the plates to allow the plates to slide over the core, wherein at least one of the upper and lower curved surfaces of the core comprises an annular channel adapted to receive the annular rib;
    wherein the annular rib cooperates with the annular channel to retain the core between the plates when the plates slide over the core; and
    wherein the lateral portions of the upper and lower plates are adapted to contact one another during sliding movement of the plates over the core.

13. The prosthetic disc of claim 12 wherein the annular channel and the annular rib are located between a central axis of the relevant curved surface and an outer periphery thereof.

14. The prosthetic disc as in claim 12, wherein the rib locates within the channel with clearance.

15. The prosthetic disc as in claim 14, wherein at a limit of sliding movement the rib abuts against a side of the channel.

16. The prosthetic disc as in claim 12, further including at least one fin extending from each of the outer surfaces of the plates.

17. The prosthetic disc as in claim 16, wherein each fin is oriented in a straight line in an anterior-posterior direction.

18. The prosthetic disc as in claim 16, wherein each fin is rotated away from an anterior-posterior axis of the disc.

19. The prosthetic disc as in claim 12, wherein the lateral portions of the upper and lower plates comprise lateral edge portions.

20. The prosthetic disc as in claim 12, wherein the outer surfaces of the plates are textured to enhance attachment of the plates to the vertebrae.

21. The prosthetic disc as in claim 20, wherein the textured surfaces comprise multiple serrations.

22. The prosthetic disc as in claim 12 wherein the lateral portions of the upper and lower plates comprise outer peripheries of the curved surfaces and wherein the plates are adapted to contact one another at the outer peripheries of the curved surfaces.

* * * * *